| United States Patent [19] | [11] | 4,412,002 |
|---|---|---|
| McAleer et al. | [45] | Oct. 25, 1983 |

[54] PROCESS FOR PREPARING HEPATITIS A VIRUS

[75] Inventors: William J. McAleer, Ambler; Fred J. Bailey, Hatfield; Henry Z. Markus, Wincote, all of Pa.

[73] Assignee: Merck & Co., Inc., Rahway, N.J.

[21] Appl. No.: 352,667

[22] Filed: Feb. 26, 1982

[51] Int. Cl.$^3$ .................................................. C12N 7/08
[52] U.S. Cl. .................................. 435/237; 435/235; 424/89
[58] Field of Search .................. 424/89; 435/235, 237, 435/241

[56] References Cited

U.S. PATENT DOCUMENTS 3,948,725  4/1976  Irie ........................................ 435/241
4,164,566  8/1979  Provost et al. ........................ 424/89

OTHER PUBLICATIONS

Provost et al.–PSEBM, vol. 160 (1979), pp. 213–221.

*Primary Examiner*—Sam Rosen
*Attorney, Agent, or Firm*—Donald J. Perrella; Hesna J. Pfeiffer

[57] ABSTRACT

Hepatitis A virus is harvested from persistently infected cells, the cells are then trypsinized, replanted and a second harvest of hepatitis A virus is obtained. The cells can be trypsinized and replanted and harvested indefinitely.

4 Claims, No Drawings

PROCESS FOR PREPARING HEPATITIS A VIRUS

BACKGROUND OF THE INVENTION

The propagation of hepatitis A virus in cell culture in vitro has been described by Provost et al., Proc. Soc. Exp. Biol. Med. 160, 213-221 (1979), and also in U.S. Pat. No. 4,164,566. In these prior art techniques, however, the infected cells are disrupted to harvest the virus and the virus is then used to infect a new culture of uninfected cells in vitro.

OBJECTS OF THE INVENTION

It is an object of the present invention to provide an improved method for growing hepatitis A virus in cell culture in vitro. Another object is to provide a method for passaging cells already infected with hepatitis A virus. Still another object is to provide a method for growing hepatitis A virus in cell culture in vitro without the necessity of maintaining stocks of both cells and viruses. A further object is to provide a method for growing hepatitis A virus in cell culture in vitro in shorter time and with higher yield. These and other objects of the present invention will be apparent from the following description.

SUMMARY OF THE INVENTION

Hepatitis A virus is harvested from persistently infected cells, the cells are then trypsinized, replanted and a second harvest of hepatitis A virus is obtained. The cells can be trypsinized and replanted and harvested indefinitely.

DETAILED DESCRIPTION

The present invention relates to the cell culture in vitro of hepatitis A virus and, more particularly, to a method whereby persistently infected cells are passaged and repeatedly harvested.

According to the present invention a cell culture system susceptible of infection by hepatitis A virus such as, for example, MK-2 cells, is grown in vitro for a period of time sufficient to form a cell sheet, and then infected with hepatitis A virus. After the cells are infected, they are harvested by trypsinization and replanted in tissue culture flasks. After the cell growth is reestablished, the cells are trypsinized, and again replanted. This procedure can be repeated indefinitely.

The following examples illustrate the present invention without, however, limiting the same thereto. All temperatures are expressed in degrees Celsius.

EXAMPLE 1

A suspension containing 25 ml of LLC-MK-2 cells at a concentration of $10^5$ cells/ml in medium 199 containing 2.0% of bovine fetal serum was planted in 75 $cm^2$ flasks and incubated at 35°. On day 7, the cell sheet was infected with hepatitis A virus (3 ml of a 1:5 virus dilution). Two weeks later the virus infected cells were harvested by trypsinization. One-half of the cells were frozen with 5% dimethylsulfoxide in liquid nitrogen as a stock virus-cell preparation. The second half was subcultured into 75 $cm^2$ flasks as described previously.

The virus infected cells were subcultured on a biweekly basis. At each passage two flasks were harvested for antigen by freeze-thawing and sonication. The antigen titers were evaluated and compared to titers obtained in a conventional preparation where uninfected cells were pregrown for one week, infected with hepatitis A virus and then harvested two weeks later. Part of the harvest was used to infect another virus-free cell sheet. The results of these experiments are summarized in the following table.

| | Titer* | |
|---|---|---|
| Passage | Persistently Infected Cells | Control Cells |
| 1 | — | 19 |
| 2 | 55 | 21 |
| 3 | 32 | 11 |
| 4 | 26 | 14 |
| 5 | 31 | 39 |

*P/N ratios of a radioimmuno assay.

EXAMPLE 2

Supernatant samples were taken at each passage 7 days post infection for control flasks and 7 days post planting for persistently infected MK-2 cells. Results are summarized in the following table:

| | Titer* | |
|---|---|---|
| Passage | Persistently Infected Cells | Control Cells |
| 1 | 10 | 6 |
| 2 | — | 10 |
| 3 | 14 | 6 |
| 4 | 11 | 6 |
| 5 | 9 | 9 |

*P/N ratios of a radioimmuno assay.

EXAMPLE 3

Persistently infected MK-2 cells were planted in 75 $cm^2$ flasks, and incubated at 35° C. Supernatant fluids were harvested every 7 days and replaced with fresh medium. Supernatant fluids were tested for virus content. Results are summarized as follows:

| Days Post Planting | Titer* |
|---|---|
| 7 | 10 |
| 14 | 34 |
| 21 | 27 |
| 28 | 29 |
| 35 | 23 |
| 42 | 17 |
| 49 | 26 |

*P/N ratio of radioimmuno assay.

EXAMPLE 4

A steam sterilized 3S100 Vitafiber ® (Amicon) hollow fiber capillary unit was planted with 2 ml of the frozen stock virus cell preparation from Example 1. The unit was connected to a 1 liter circulating sterile culture medium 199 with 0.2% bovine fetal serum and neomycin. The capillary was placed in a $CO_2$ incubator at 35° and the culture medium was circulated at 5 ml/minute by a peristaltic pump. Cell growth was monitored by glucose utilization and viral antigen production in the extracapillary fluid was determined by a quantitative radioimmuno assay. The following table summarizes the results that were obtained.

| Age of Culture (Days) | Hepatitis A Antigen (ng/ml) |
| --- | --- |
| 7 | 18 |
| 14 | 30 |
| 21 | 86 |
| 28 | 202 |
| 35 | 154 |
| 42 | 256 |
| 49 | 194 |

What is claimed is:

1. A method of growing hepatitis A virus in vitro in a cell culture susceptible to infection by hepatitis A virus comprising trypsinizing a culture of susceptible cells persistently infected with hepatitis A virus, replanting at least part of the trypsinized cells at least one additional time, and harvesting hepatitis A virus from at least some of the replanted cells.

2. A method according to claim 1 wherein the replanted cells are trypsinized, at least part of the trypsinized cells are replanted, and hepatitis A antigen is harvested from at least some of the replanted cells.

3. A method according to claim 1 wherein at least part of the trypsinized cells are replanted and at least part of the replanted cells are replanted and reharvested at least one additional time.

4. A method according to claim 1 wherein the cells are incubated for a period of time sufficient to form a cell sheet before being infected with hepatitis A virus.

* * * * *

REEXAMINATION CERTIFICATE (578th)
United States Patent [19]
McAleer et al.

[11] B1 4,412,002
[45] Certificate Issued Oct. 7, 1986

[54] PROCESS FOR PREPARING HEPATITIS A VIRUS

[75] Inventors: William J. McAleer, Ambler; Fred J. Bailey, Hatfield; Henry Z. Markus, Wincote, all of Pa.

[73] Assignee: Calgon Corp., Pittsburgh, Pa.

Reexamination Request:
No. 90/000,645, Oct. 9, 1984

Reexamination Certificate for:
Patent No.: 4,412,002
Issued: Oct. 25, 1983
Appl. No.: 352,667
Filed: Feb. 26, 1982

[51] Int. Cl.$^4$ .............................................. C12N 7/02
[52] U.S. Cl. ................................... 435/235; 424/89; 435/237
[58] Field of Search ............................... 435/235, 237

[56] References Cited
PUBLICATIONS

Frosner et al.–Workshop of the Virology Section of the DGHM, Zentralblatt Fhur Bacteriologie, Parasitenkunde Infekitionskrankheiten Und Hygine, vol. 248 (1) (1980) pp. 15–16.

*Primary Examiner*—Sam Rosen

[57] ABSTRACT

Hepatitis A virus is harvested from persistently infected cells, the cells are then trypsinized, replanted and a second harvest of hepatitis A virus is obtained. The cells can be trypsinized and replanted and harvested indefinitely.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-4 are cancelled.

* * * * *